United States Patent [19]
Small et al.

[11] Patent Number: 5,997,849
[45] Date of Patent: *Dec. 7, 1999

[54] THERMOCHROMIC INK FORMULATIONS, NAIL LACQUER AND METHODS OF USE

[75] Inventors: Lyle D. Small, Colorado Springs, Colo.; Gerald Highberger, Linden, N.J.

[73] Assignee: Chromatic Technologies, Inc., Ithaca, N.Y.

[*] Notice: This patent is subject to a terminal disclaimer.

[21] Appl. No.: 08/824,656

[22] Filed: Mar. 24, 1997

Related U.S. Application Data

[63] Continuation of application No. PCT/US95/12510, Sep. 29, 1995, which is a continuation-in-part of application No. 08/175,098, Dec. 29, 1993, abandoned.

[51] Int. Cl.$^6$ .............................. A61K 7/04; C09D 11/00
[52] U.S. Cl. ......................... 424/61; 106/20 R; 106/23 R
[58] Field of Search ........................... 424/61; 106/20 R, 106/23 C; 132/73

[56] References Cited

U.S. PATENT DOCUMENTS 5,591,255  1/1997  Small et al. .............................. 106/21

*Primary Examiner*—Thurman K. Page
*Assistant Examiner*—Sharon Howard
*Attorney, Agent, or Firm*—Brown, Pinnisi & Michaels, P.C.

[57] ABSTRACT

A method of making a solvent based ink formulation which includes a thermochromic pigment, wherein the pigment being formed of microcapsules, includes drying a slurry that contains the pigment to a solids concentration between 80% and 95%, mixing the dried slurry in an appropriate mixing base, and adding any desired ink components to the base formulation. Each microcapsule contains a reversible thermochromic coloring material which exhibits a visible change in color between a first color state and a second color state in response to a change in temperature. Acceptable ink components include a gel vehicle, a free flow vehicle, a drying agent, a lithographic varnish, an ink wax, a polyester vehicle, a polyglycol solvent, a colloidal dispersion resin, water, and a defoamer.

16 Claims, 1 Drawing Sheet

THERMOCHROMIC INK FORMULATIONS, NAIL LACQUER AND METHODS OF USE

CROSS REFERENCE TO RELATED APPLICATIONS

This application is a continuation of copending application PCT/US95/12510, filed Sep. 9, 1995, which claims priority from application Ser. No. 08/175,098 filed Dec. 29, 1993 entitled "Thermochromic Dye Formulations", now abandoned.

FIELD OF THE INVENTION

The invention pertains to the field of thermochromic dye formulations. More particularly, the invention pertains to thermochromic dye formulations for inks used in lithographic, flexographic or rotogravure printing techniques or thermochromic dye formulations for lacquers.

BACKGROUND OF THE INVENTION

Thermochromic and photochromic encapsulated dyes were developed a number of years ago, and primarily incorporated into plastic or textile colorants for wide commercial applications (e.g. the "mood ring" and thermochromic dyed clothing). Thermochromic dyes go through a color change over a specific temperature range. The dyes currently available change from a particular color at low temperature to colorless at a high temperature (e.g. red at 85° Fahrenheit and colorless at above 90° Fahrenheit). The color change temperature can be controlled, such that the color-change can take place at different temperatures (eg. just below a person's external body temperature so that a color change occurs in response to a human touch). The thermochromic dye manufacturers are able to manipulate the critical temperature for the color change.

The variability in the dyes is a result of the process used in their manufacture. One technique used to produce the thermochromic encapsulated dye is to combine water, dye, oil, and melamine formaldehyde and shake to create a very fine emulsification. Because of the properties of the compounds, the oil and dye end up on the inside of the capsule and the water ends up on the outside, with the melamine formaldehyde making up the capsule itself. The encapsulation, melamine formaldehyde, is a thermo set resin similar to formica. The substance is very hard and will not break down at high temperature. It is almost entirely insoluble in most solvents, but it is permeable.

This idea is important to success with respect to product development using this material. A key factor is exposure. In other words, what the encapsulated dye "sees" is of the utmost importance, and will be a determining factor in the extent of deterioration in the color change characteristics of the material. It is this effect that has heretofore prevented the incorporation of thermochromic dyes in many types of ink and lacquer products.

Over the years, discoveries have been made in microencapsulation techniques, as well as in thermochromic chemistry, that have broadened the potential application of these materials. Most thermochromic dyes consist of an internal phase of "liquid phase" which changes color when it reaches a certain temperature, and the external or 'solid phase' which protects the internal phase. Originally, the product had a size of 5 to 15 microns, could only change color at one temperature, and would deteriorate quickly in the sun. The size of the capsule has decreased, (0.5 to 5.0 microns), and ingredients have been added to the liquid phase that greatly improved color fastness and allow one to adjust the temperature at which the color change takes place. These improvements make it possible to incorporate the thermochromic into ink vehicles, and to print them using different methods. The problem is that, even though these materials have been greatly improved, they are still very sensitive to external changes in environment.

In order to overcome the shortcomings of the product as it now stands, we began our research by closely examining the chemical and mechanical aspects of the ink manufacturing, thermochromic chemistry, and printing methods relevant to our problem. Since the surface of the capsules is very different compared to the surface of traditional pigments, the interface of the vehicle and the capsule surface were the main point of focus. There are several types of ingredients that are traditionally added to an ink formulation. The combination of all the ingredients in an ink, other than the pigment, is called the vehicle. The vehicle carries the pigment to the substrate and binds the pigment to the substrate. The correct combination of vehicle ingredients will result in the wetting of an ink. This wetting means that the vehicle forms an absorbed film around the pigment particles. The main ingredient in an ink is the binder. It can be a resin, lacquer or varnish or some other polymer. Its characteristics may vary depending on the type of printing being done and the desired final product. The second main ingredient is the colorant itself. The remaining ingredients are added to enhance the color and printing characteristics of the binder and the colorant. These might include reducers (solvents), waxes, surfacant, thickeners, driers, and/or UV inhibitors.

Those involved with attempting to solve this problem in the past have taken a traditional ink-making approach to finding a solution. To our knowledge the manufacturers of the thermochromic capsules have left the problem of creating the ink product to ink chemists. Ink chemists that we have spoken with have treated the thermochromic capsules as though they were normal pigments. Their resulting ink would not flow on the rollers, and would not change colors, if there was any color at all on the printed paper. The conclusions drawn from such an approach is that the rollers are crushing the thermochromic capsule. This hypothesis is false. We have studied the process by which it is manufactured and the chemicals used in that process. We then studied its behavior in several varied environments.

U.S. Pat. No. 4,421,560 entitled "Thermochromic Materials" granted to Kito et al. and U.S. Pat. No. 4,425,161 entitled "Thermochromic Materials" granted to Shibahashi et al. both state that thermochromic inks can be made with "conventional additives used to improve conventional printing inks." Furthermore, U.S. Pat. No. 4,421,560 states that the inks can include many solvents and compounds that the applicants have discovered destroy the color change characteristics of thermochromic pigment currently commercially available. (eg. alcohols, ketones, amino resin, petroleum solvents, etc.) These patents fail to teach that many of the solvents and compounds commonly used to make printing inks are harmful to the thermochromic dye and therefore fail to teach the necessary principles to create a thermochromic printing ink that works.

Thermochromic screen inks have been sold previously by Liaison Printing, Inc., and these inks were all of neutral pH inherently or the pH was adjusted to be neutral, however, the harmful solvents were not removed and these inks only had a shelf life of about 6 weeks.

Therefore, it is an object of the present invention to teach ink formulations and a method of correcting formulations that normally destroy the color change properties of thermochromic dyes such that the thermochromic dye can be added to the formulation or corrected formulation and maintain its color change properties.

The patents referred to above also state that it is possible to use the thermochromic dyes in inks for lithographic printing but provide no instructions for how to use the inks. Lithography depends upon the separation of oil and water. The oil is the ink and the water is the fountain solution. The fountain solution is acidic to minimize the emulsification of ink. The higher the pH the more scumming occurs; i.e. the movement of ink into areas of the image that are supposed to by free of ink. The acid and other components in fountain solutions destroy the color change characteristics of the thermochromic pigments.

Therefore, it is another object of the present invention to teach lithographic, flexographic or rotogravure printing techniques for thermochromic inks.

U.S. Pat. No. 4,920,991 teaches a thermochromic artificial nail that has a thermochromic layer embedded in acrylic-resin. This means that a customer must purchase premade artificial nails with the desired color-change characteristics. The user can not apply the thermochromic layer herself and experiment with different background colors.

Therefore, it is another object of the present invention to teach formulations for thermochromic nail lacquers.

SUMMARY OF THE INVENTION

The present invention comprises a series of discoveries related to the problems associated with the printing of microencapsulated thermochromic dyes, including the ink vehicle into which they are incorporated, the printing process and the printing substrate.

The present invention includes formulations that can be used to create inks including thermochromic material. The inks themselves avoid many of the standard solvents and materials in inks that have been discovered to be harmful to thermochromic pigments. The acid content of the ink vehicles has also been reduced as much as possible.

These inks can be used with traditional offset presses and plates, however, a novel method of using these presses is taught in this application. To print with these inks in an offset press, all harmful solvents must be cleaned from the press as well as any residual standard printing ink. The press should be run with a fountain solution that is does not harm thermochromic pigment (eg. distilled water). Traditionally, all lithography (offset printing) uses fountain solution to enhance the separation of the oil (ink) and "water" (fountain solution). Fountain solutions are very expensive and hazardous to the environment. Heretofore, it was unknown that high definition lithography could be accomplished using distilled water as a fountain solution. Therefore, this technology is a major step forward in the art of lithography in general, as well as a specific development of a method of printing with thermochromic inks for the first time.

One aspect of the present invention is the discovery of a method of correcting these formulations to allow the addition of thermochromic dyes. The method comprises making a series of adjustments to the formulations prior to adding thermochromic dye. Certain solvents and other compounds destroy the dye, therefore any aldehydes, ketones, and diols should be removed from the formulation and if needed they should be replaced with solvents which do not adversely effect the thermochromic pigment. Solvents having a large molecular weight (i.e. greater than 100) generally are compatible with the thermochromic pigments. Secondly, the acid content of the formulation must be adjusted low (i.e. acid number below 20) or adjusted to be neutral (i.e. 6.5–7.5 pH). These two adjustments will allow the thermochromic dyes to be added to the formulation without a loss of its color change properties.

DESCRIPTION OF THE PREFERRED EMBODIMENT

Figure 1:
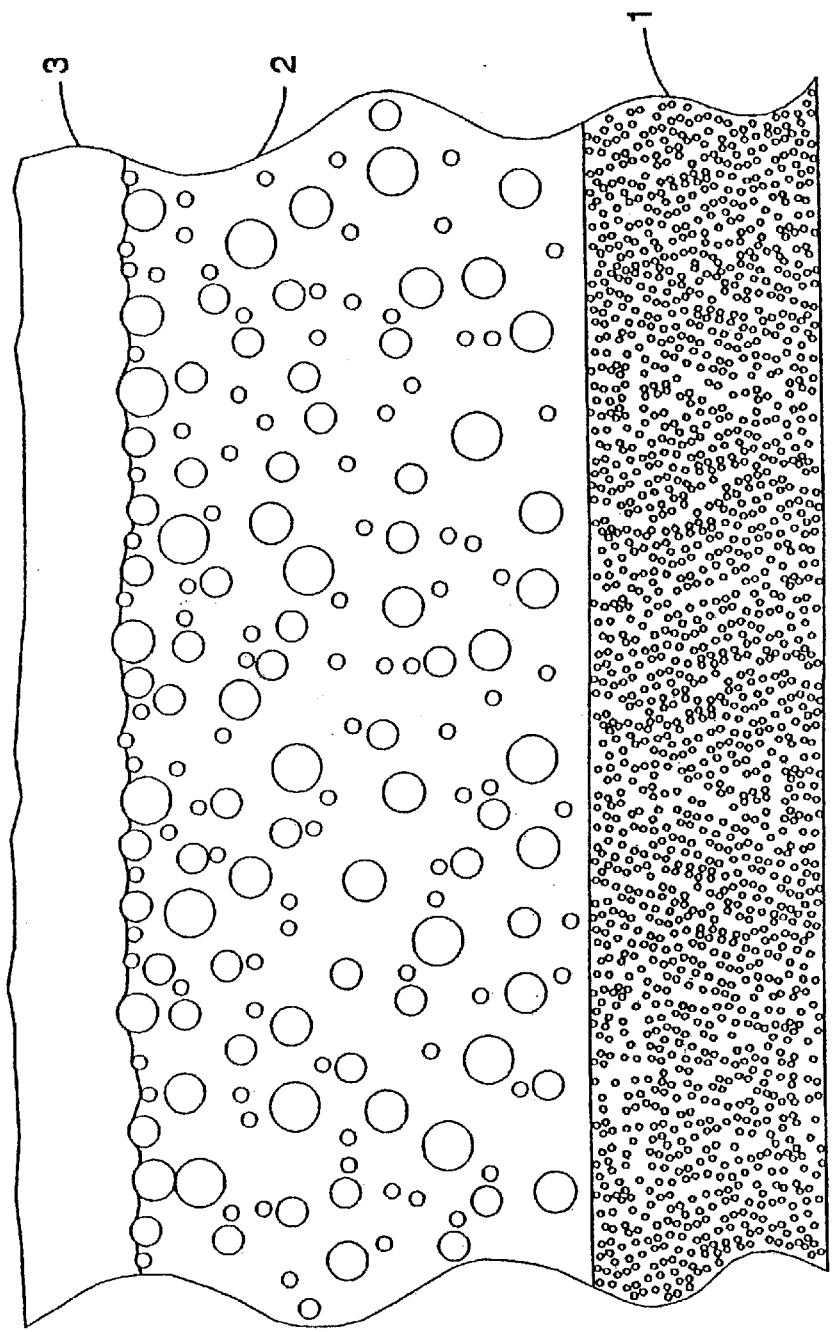
FIG. 1 shows a representational view of a three layer system for nail polish that includes a thermochromic layer.

Thermochromic dyes can be purchased from any one of a number of suppliers. The present invention was developed using dyes purchased from the following suppliers: Pilot Inc. and Davis Liquid Crystal Inc. The other reagents described herein are standard and can be purchased from most chemical supply companies The following detailed description includes a general discussion of the problems associated with thermochromic dye formulations. The principles of reactivity, pH, permeability, polarity, and reactivity are important to understanding this technology. Also taught fully herein are new formulations using thermochromic dyes made according to the general principles. Printing inks for lithographic, flexographic and rotogravure process are taught with specific examples for each. Also taught herein is a thermochromic nail lacquer.

General Principles

Reactivity is very difficult to explain because it is itself often ambiguous. It is, however, the cornerstone of an understanding of these materials. The extent to which molecules will react with each other is influenced by the pH of the surrounding medium, the permeability of the capsule, the polarity of all compounds involved, the solubility of the capsule and the reactivity of the compounds. The goal of finding an appropriate medium for the thermochromic capsules, is to reduce the reactivity between that medium and the capsules to zero, or at least to a low enough level that the reactivity will not influence the characteristics of the dye for an extended period of time.

Water has a neutral pH. The thermochromic dye is often sold in a slurry of encapsulated dye in a water base. It happens that the pH of this slurry is neutral. All aqueous media, therefore, that the dye is placed in must be at a neutral pH (±0.5). This variability is caused by the reactivity of certain solutions at a given pH. Therefore, some empirical work may be needed to determine what pH in this range is best, but when the thermochromic dye is added to a formulation that has a pH outside this range, the color change properties are almost always lost. This is an irreversible effect and therefore, it is important to adjust the pH prior to adding the thermochromic dye.

As previously mentioned, the capsule has pores in it. The rate at which substances move through the capsule into the core, is described in terms of permeability. The more permeable a partition, the more quickly something will move through it. At this point it should be stated that all of these principles are related to one another in integral ways. They must be considered in relationship to one another in order to be effective in solving the problems we are discussing.

In simple terms, polarity is defined by the uneven distribution of the outer electrons within a given molecule. The more uneven this distribution is, the more polar the molecule is said to be. By the same token, non-polar molecules have a relatively even distribution of electrons throughout the molecule. In general, highly polar molecules will react more with the dye and capsule than non-polar molecules. (There are exceptions to this rule. Fortunately, the only serious exception is water, which is highly polar but obviously does not have an adverse effect on the dye.)

Solubility, is how easily something dissolves in the presence of a given solvent. If something (like salt) is highly soluble in water, for instance, then water will dissolve it completely if enough water is present. Temperature is usually directly proportional to solubility. (as temperature increases, solubility will increase.) This is important because the capsule itself, though very hard, is soluble to an extent. This solubility is characterized by what is known as the "solubility parameter". This parameter describes how much a material will swell in the presence of different solvents. This swelling will directly impact the characteristics of the reaction potential within the capsule, as well as making the capsule more permeable, both of which adversely affect the material. Solvents must therefore be chosen with great care.

The goal is to minimize the interactions between the dye and its surroundings. The capsule is the major part of this. The capsule is hard, non-polar, thermally very stable (it won't melt), and relatively impermeable. The infiltration of compounds through the capsule must be stopped or slowed to the point that the characteristics of the dye are not effected. Shelf-life is an issue and must be considered in the context of the above principles. Almost any solvent will penetrate the capsule given enough time. The question that each person using this technology will need to ask themselves is: What is an acceptable shelf-life for the product we are developing and will our formulation give us the desired result?

We already know that the capsules and the dye they contain will not react with water. Why not? It is a highly polar, small molecule. Why doesn't it destroy the dye's properties? The fact that it does not react with the capsule or the dye gives us several hints about the material. The most important principle to learn from this is that there must be certain combinations of characteristics present for a substance to effect the dye.

Melamine formaldehyde is not soluble in water. The water is not absorbed by it, so the capsules is impermeable to water. Water has a greater affinity for itself than it has for most other substances. Using the above principles and the knowledge that we have of water outlined above, we can deduce many things that will help us in creating inks, dyes, and other media that are essentially unreactive with the capsule or dye.

Solvents

There are three types of solvents to avoid when working with this material. There are four classes of solvents known as aldehydes, ketones, diols and aromatic compounds that should not be used when developing products. No ink will work with these types of solvents in them. There are obviously other solvents that will not work, but one must try them before you will know for sure.

Therefore the first step in creating a thermochromic dye formulation of the present invention is to remove any harmful solvents from the formulation. If needed non-harmful solvents can be used to replace the solvents that have been removed. The best solvents to use will be those that have low reactivity, are large molecular weight (i.e. over 100), and which are relatively non-polar. One solvent that fits this category is cyclohexane. It has low toxicity and works well.

Adjusting the Acid Content

The second step is the most effective and most straight forward. All water-base inks that are used must be pH adjusted prior to addition of thermochromic pigment. As mentioned above, the pH should be neutral unless observation indicates that a different pH is required. To achieve the correct pH, one must use a good proton donor or acceptor, depending on whether the pH must be adjusted up or down. To raise the pH, HCl is used, to lower it, the best proton acceptor so far is KOH. These two chemicals are very effective and do not seem to impart undesirable characteristics to the medium. (In other words, K+ and Cl– do not seem to harm the thermochromic pigment.) Use pH paper to determine the pH. Remember not to add pigment before the pH and all other characteristics for that matter are correct in the ink itself. The most effective pH has been 7.0, however, some tolerance has been noted between 6.0 and 8.0. A pH below 6.0 and above 8.0 has almost always immediately destroyed the pigment.

The acid value is defined as the number of milligrams of a 0.1N KOH solution required to neutralize the alkali reactive groups in 1 gram of material under the conditions of ASTM Test Method D-1639-70. It is not yet fully understood how non-aqueous substances containing acid effect the thermochromic, but high acid number substances have inactivated the thermochromic pigments. Generally, the lower the acid number the better. To date ink formulations with an acid value below 20 and not including the harmful solvents described above have worked well. Some higher acid value formulations may be possible but generally it is best to use vehicle ingredients with low acid numbers or to adjust the acid value by adding a an alkali substance. The greatest benefit of a neutral or low acid value vehicle will be increased shelf life.

Buffers have been used historically in inks to minimize the effects of the fountain solution on pigment particles. This is one possible solution to the potential acidity problem of the varnishes. One ingredient often used as a buffer is cream of tartar. A dispersion of cream of tartar and linseed oil can be incorporated into the ink. The net effect is that the pigments in the ink are protected from the acidic fountain solution.

Mixing

The thermochromic inks are sold in two ways: 1) as a dry powder and 2) in a water based slurry. Mixing systems have been developed for both slurry and powder that will allow for consistent and well dispersed pigment.

Drying Technique

The aqueous slurry can be used to make solvent based ink formulations by drying of the slurry first.

In traditional ink manufacturing, there is a technique known as flushing. Many traditional pigments come in slurry form, similar to that of the thermochromic capsules. "Flushing" in traditional manufacturing, means to press most of the water out of the slurry to form what is called a press cake which is then "flushed" into a mixing varnish. The press cake is about 25–40% solids. Because of the hydrophobic properties of the pigment and the varnish, the pigment is mixed into the varnish and away from the water. The water separates from the varnish and is left behind. Flushing with the thermochromic capsules does not work. All of the water stays in the varnish rather than separating. We believe it does this because of the waters attraction to the surface of the capsule.

The thermochromic encapsulated dye is purchased in slurry form from Davis. This slurry is placed in a forced air dryer, where the temperature is maintained at between 100 and 150 degrees F. When the slurry reaches the "stiff clay" stage, at about 80% to 95% solids, the slurry is removed and incorporated into a varnish. The varnish is mixed until smooth and the remaining ingredients are than added to this mixture. This mixture is then put over the mill between one and fifteen times, making the final product. We have tried to mix our inks with a "press cake" which has 80 to 95 percent solids so that the water does not alter the properties of the ink too severely.

We have found that using this mixing technique, we can achieve good dispersion and much improved color intensity over using the dried thermochromic capsules. Not only is it difficult to get the dried capsules to disperse appropriately, but the drying process used by the manufacturer apparently destroys between 10% and 30% of the colorant.

By using an ink mill, on low pressure (0.0 to 100.0 psi), an acceptable grind can be achieved without further damage to the thermochromic capsule. Several passes (1 to 15) may be necessary to disperse the thermochromic colorant sufficiently, but the fewer passes on the mill the better in terms of damage to the material. The number of passes on the mill can be reduced by more vigorous pre-mixing.

Ultrasound Technique

If the ink requires powder to make it, there may be a problem with dispersion because, in the drying process, the capsules form aggregates that are very difficult to break up. Over stirring or the wrong type of stirring will damage or denature the dye.

The technique that has been developed to solve this problem is simple, effective and inexpensive. The first step is to add the powder to an appropriate solvent. For the nail lacquer, the solvent used for this step is the same as the same solvent used in the lacquer itself, Butylacetate. With the rest of the inks, either cyclohexane or other aromatic compounds can be used. The solids content of this mixture should be about the same as for the water base slurry of 50% solids. Once the solvent and the powder are combined, the container with the mixture is submerged in an ultrasound bath. The vibration breaks up the aggregates and also conditions the capsule for its addition to the rest of the medium.

General Procedures for Mixing Formulations

For the applications discussed herein, the technique is essentially that of adding pigment to different media to attain a desired result; that of mimicking the visual appearance of normal pigments while trying to add the dimension of thermal activity to its properties.

In order to add normal pigment to ink, dye, or lacquer, the pigment itself is ground into the base. This disperses the pigment throughout the base. Since the pigment is usually a solid crystal with a diameter no larger than 1.0 microns this grinding is not difficult to do. The eye cannot see particles that size, so the pigment will give the base a solid color. The addition of more pigment simply intensifies the color. Since the pigment has a very intense color only about 10% of the final ink is made up of normal pigments. Also, the normal pigment itself is relatively impervious to the effects of solvent and pH.

Others have used thermochromic dyes, however, these attempts have focused simply on the addition of thermochromic capsules to an ink base at random and observing whether or not the capsules maintain their original color-changing properties. There are Plastisol and water-based UV inks that are now on the market that change color with temperature. The reason these have been successful, is because the inks do not contain any chemicals or chemical properties that will adversely effect the capsule or dye. No one realized why it was possible to use thermochromic pigments in solvent based inks and to use them with a traditional offset press until the present invention.

In general, the present invention teaches the following procedure for making formulations with thermochromic dyes. If in slurry form, and is intended for addition to a water base ink, the water is removed to give slurry between 80% and 95% solids. This is then mixed with an appropriate ink vehicle and milled.

A base for an ink is developed using off the shelf ingredients. The ink will incorporate, where possible, and compatible with the ink types, solvents with molecular weights larger than 100 and avoid all aldehydes, diols, and ketones, and aromatic compounds. Selection of the ingredients is critical. The important considerations with respect to the ingredients within the ink vehicle deal with the reactivity of these ingredients with the thermochromic capsule and its contents.

One possible explanation for deterioration, is that there may be a breakdown of the capsule by molecules contained in the ink vehicle. This would allow deleterious compounds that would otherwise be kept out to subsequently enter the capsule and alter the chemistry of the liquid phase. This phenomenon would depend on the reactivity of the particular molecule in the vehicle. We have carefully chosen varnishes, reducers, extenders, and driers with low reactivity in order to minimize their influence on the capsule. These additives will also extend the life of the product over time.

Another explanation for the breakdown may lie in cross-capsule interactions between vehicle molecules and the liquid phase. Due to the long-chain nature of the compounds found in ink vehicles, there may be reactive portions of the molecules that can fit through the pores of the capsule and interact with the liquid phase and denature it through this interaction. Since the behavior of the thermochromic is related to its shape and the location of its electrons at given temperatures, a minor impact due to outside molecules, could have a large impact on the characteristics of the liquid phase. Molecules that cannot fit through the capsule pores, may have reactive portions that could protrude into the capsule and thereby influence the liquid phase.

Ketones, Diols, and Aldehydes must be minimized, as well as most mineral spirits, excluding cyclohexane and other chemically similar compounds. Ammonia, and other highly reactive compounds must also be avoided. The lower the amounts of these compounds, the better the performance of the thermochromic and the longer the shelf life of the product.

One very important step is to adjust the pH or lower the acid value of the ink base before the pigment is added. This can be done by ensuring that each individual component of the base is at the correct pH or acid value or by simply adding a proton donor or proton acceptor to the base itself prior to adding the pigment. The appropriate specific pH is generally neutral, or 7.0. The pH will vary between 6.0 and 8.0 depending on the ink type and the color and batch of the pigment.

Once the slurry and the base have been properly prepared, they are combined. The method of stirring should be low speed with non-metal stir blades. An ink mill may be used so long as the mill pressure is set low enough to avoid harming the microcapsules. Other additives may be incorporated to keep the pigment suspended. The ink should be stored at room temperature.

Most thermochromic dyes undergo a color change from a specific color to colorless (i.e. clear). Therefore, layers of background colors can be provided under thermochromic layers that will only be seen when the thermochromic layer changes to colorless. If an undercoat of yellow is applied to the substrate and then a layer containing blue thermochromic dye is applied the color will appear to change from green to yellow, when what is really happening is that the blue is changing to colorless.

The Substrate

One issue that must also be addressed at this stage is the chemical characteristics of the material printed on. This area of focus has essentially one component. It must be remembered that whatever surface or substrate one prints to, that substrate must have the same characteristics that the ink base has. That is, all substrates should be neutral in pH, and must not impart any chemicals to the capsule that will have a deleterious effect on it. The greatest concern is with paper. Many types of paper produced today have relatively low pH and could impact the capsule. Low pH could cause serious deterioration in a matter of weeks. If quality control is to be maintained, this aspect of the chemistry should be taken into consideration. Use neutral paper whenever possible.

Specific Formulations

Examples of specific formulations of thermochromic dye formulations are provided below using the principles and techniques taught above.

An aqueous slurry of thermochromic pigment containing approximately 50% pigment solids is dried in an oven at 100–150 degrees F. to achieve a solids concentration of 80%–95% by weight of thermochromic pigment. Solid levels below 80% introduce excess water into finished ink formulations and make it difficult to properly disperse the pigment in the ink vehicle, and generally solids concentrations above 90% are preferable. Solids greater than 95% result in strong agglomeration of the pigment particles and make dispersion difficult, however, drying to solids concentrations up to 98% has worked. The consistency of the dried pigment slurry will vary between that of wet clay and nearly dry kernels and flakes. This material is then combined with a grinding/mixing varnish formulated for the dispersion of dry pigment or presscake, which typically is high in tack and viscosity, may contain a significant proportion of alkyd resin, and have an acid value not to exceed 15.

EXAMPLE 1

The dried pigment slurry is added to the vehicle under mechanical agitation in an amount to achieve a weight/weight ration of 1 part of pigment solids to 1 part of vehicle. Agitation may be provided by various types of mixers, however, the final viscosity of the mix will be quite high, and the flow properties of the dispersion may be poor, therefore, a dual axial, planetary, or turntable-type mixer is recommended. Care must be taken to ensure that the thermochromic pigment particles are not ruptured during the dispersion. A three-roller ink mill may also be used for making the dispersion, but the rollers must be set in a loose manner, so as not to rupture the pigment particle. Agitation is continued until a smooth glossy dispersion is obtained. The grind rating of the finished dispersion, as determined on a NPIRI Grind Gauge, should be a minimum of 3. This mix will be referred to below as Offset Ink Base. The acid value of the vehicle used in this ink should not exceed 40.

EXAMPLE 1-A

Offset Ink Base is combined with other ink components to produce a Quick-Set lithographic ink as follows: (the acid value of the vehicles used should not exceed 15.)

| Ingredient | Weight % |
| --- | --- |
| Offset Ink Base | 75.0 |
| Quick Set Gel Vehicle | 12.5 |
| Quick Set Free Flow vehicle | 7.5 |
| 12% Cobalt Drier | 1.0 |
| 6% Manganese Drier | 1.0 |
| Ink Oil (IBP 510 deg. F.) | 3.0 |
| TOTAL | 100.0 |

EXAMPLE 1-B

To the ink described in 1-A, a finely divided microcrystalline wax, polyethylene wax, Fisher-Tropsch wax, either alone or in combination with a finely divided polytetrafluorethylene polymer, is added to the ink to improve the dry rub resistance of the dried ink film. Additions of dry wax may be made from 0.5% to 3.0%. Additions of compounded waxes may be from 1.5% to 10%, depending on the wax compound used should not exceed 15.

EXAMPLE 1-C

Offset Ink Base is combined with other ink components to produce a hard drying, high solids ink as follows:

| Ingredient | Weight % |
| --- | --- |
| Offset Ink Base | 75.0 |
| High-solids Gel Vehicle | 10.0 |
| High-solids Free Flow Vehicle | 10.0 |
| 12% Cobalt Drier | 1.0 |
| 6% Manganese Drier | 1.0 |
| Litho Varnish | 3.0 |
| TOTAL | 100.0 |

EXAMPLE 1-D

The ink described in 1-C, where wax is added to improve the rub resistance of the dry ink film in the same manner described in 1-B.

EXAMPLE 1-E

Offset Ink Base is combined with other ink components to produce an ink suitable for printing business forms and newsprint as follows:

| Ingredient | Weight % |
| --- | --- |
| Offset Ink Base | 75.0 |
| Mineral Oil Forms Gel Vehicle | 10.0 |
| Mineral Oil Forms Free Flow Vehicle | 10.0 |
| Mineral Oil | 5.0 |
| TOTAL | 100.0 |

The vehicles in this type of ink formulation would be primarily hydrocarbon resins dissolved in mineral oil. The acid value of such vehicles generally does not exceed 5, but no instance should it be greater than 15

EXAMPLE 1-F

Soya oil-based vehicles are substituted for the mineral oil-based vehicles in 1-E to produce soya-based forms and newsprint ink.

EXAMPLE 1-G

Offset Ink Base is combined with other ink components to produce a heat-set ink as follows:

| Ingredient | Weight % |
| --- | --- |
| Offset Ink Base | 75.0 |
| Heat Set Gel Vehicle | 10.0 |
| Heat Set Free Flow Vehicle | 10.0 |
| Ink Oil (IBP 470 deg. F.) | 5.0 |
| TOTAL | 100.0 |

The acid value of the vehicles used in this ink should not exceed 15.

EXAMPLE 1-H

To the ink described in 1-G, wax, as described in 1-B, is added to improve the rub resistance of the dry ink film

EXAMPLE 2

A metal decorating ink is made by dispersing the dried pigment slurry, as described in Example 1, with an oil-free polyester resin vehicle, as follows:

| Ingredient | Weight % |
| --- | --- |
| Dried Pigment Slurry | 37.5 |
| Single Component Oil-Free Polyester Vehicle | 37.5 |

These two components are mixed mechanically, as in Example 1, until a fine dispersion is achieved. To this dispersion is added

| Single Component Oil-Free Polyester Vehicle | 20 |
| --- | --- |
| Polyglyool Solvent | 5.0 |
| TOTAL | 100.0 |

EXAMPLE 2-A

Wax, as described in 1-B, is added to the ink in Example 2 to improve the rub and abrasion resistance of the dry ink film.

EXAMPLE 3

An aqueous ink for flexographic and gravure applications is made by dispersing the aqueous thermochromic pigment slurry, as supplied, before drying, into a neutralized acrylic or modified-acrylic colloidal dispersion resin, by adding a volatile base, such as ammonium hydroxide, to neutralize and therefore solubilize, the resin, as follows

| Ingredient | Weight % |
| --- | --- |
| Colloidal Dispersion Resin (40% Solids) | 40.0 |
| Pigment Slurry | 50.0 |
| Water | 9.0 |
| Defoamer | 1.0 |
| Ammonium Hydroxide | to neutrality |

The colloidal acrylic resin used in this formulation should have a maximum acid value of 80. The amount of base added should not exceed that needed to neutralize the resin.

There are many possible vehicles and resins in the market that will work in these formulations. Also, many variations of each individual formula are possible, and probably necessary, to adjust color, color strength, and the working properties of each type of ink. The formulations presented above are meant to be typical, not absolute.

Nail Lacquer

As with inks, pigments are ground into lacquer. One main aspect of nail lacquer is that many shades are necessary. These different shades are attained by combining different pigments into the same lacquer. By using the different pigments in different ratios, thousands of colors and shades can be realized.

The chemistry of nail lacquer is straight forward. There is no impact on the normal pigments, i.e. not thermochromic, by anything within the lacquer from a chemical stand point. The three common ingredients in almost all nail lacquers are butylacetate, ethylacetate, and nitrocellulose. Some type of alcohol or aldehyde are also often used in smaller quantities. Again, the pigment size is small enough that it cannot be detected by the human eye. When the lacquer itself dries, it is clear. It is only the pigment that adds opacity and color.

U.S. Pat. No. 4,920,991 teaches a thermochromic artificial nail. This process is very similar to that used to make mugs and other plastic products. There is no attempt to incorporate thermochromics into an actual lacquer that can be applied to the nail.

As with inks the idea is to develop a nail lacquer that is similar to the non-thermochromic product in all respects, except that ours changes color with changes in temperature.

There were four main obstacles in the creation of this product. The first was finding a formulation of a lacquer that would accommodate the thermochromic capsules without destroying them. Using the principles described above this formulation was developed.

All diols, aldehydes and ketones are excluded from the formulation. Depending on the specifications of the lacquer producer, the amount of ethylacetate is reduced as much as possible. Any other substances that may harm the capsule are also excluded.

The lacquer must also be maintained at a neutral pH. This can be done by ensuring that all of the respective components of the lacquer are neutral, or by adjusting the pH once all of the ingredients, minus the thermochromic slurry, have been mixed together.

The second obstacle was that of dispersion. Once the lacquer formulation was perfected, the pigment was added, in the powder form, to the lacquer. The capsules were clumping together in large aggregates once they were added to the lacquer. This gave the lacquer a grainy look. To overcome this, cyclohexane was added to the powder and then the slurry was placed in an ultrasound bath, to disperse the capsules before adding them to the lacquer or the dried slurry form of the pigment was used as in the ink formulations. This gave a smoother look to the lacquer when applied to the nail.

The next problem was that of color. Thermochromic dyes go from a color to no color. In order to get combinations of two different colors required some sort of mixture of regular pigment with the thermochromic pigment. The problem with this was that if the thermochromic pigment is simply added directly to a colored lacquer it will greatly diminish the visible color change characteristics. This problem is solved by layering the pigments. A base color is applied to the nail and then a thermochromic layer is applied on top of the base color. Clear lacquer is used as a base. The thermochromic pigment is incorporated to make the thermochromic lacquer. By putting down a base coat of a regular pigmented lacquer, and then a thermochromic layer over that, the desired result was achieved. For instance, if a red base layer is put down with a blue thermochromic layer over the base layer, the result is a purple color in the cold and a red colored nail as it's temperature increases above a certain point. This technique was a real breakthrough because now we had the ability to create hundreds of different color combinations.

Our final problem was that of shine. The look of the nail was still rough. Since the capsules can be as much as 5 times the size of regular pigment, the finish is "bumpy", giving it the rough look. The aggregates discussed earlier made the problem even worse, so part of the problem was solved by the dispersion technique already mentioned. It was still not at the level of quality that we needed, however. The problem was overcome by adding one additional layer of clear top coat.

The final product is produced using a three layer technique illustrated in FIG. 1. A base coat of regular pigmented lacquer 1 is applied, then a middle thermochromic layer is applied 2 and a thin, clear top coat 3. The middle layer being the one that requires the special chemical and dispersion adjustments.

Printing Process

The press must first have all residual standard ink removed from it using traditional cleaning solvents. This will mean at least two good cleanings depending on the amount of ink in the press.

All of the cleaning solvent must be removed from the press using cyclohexane or other appropriate solvent. The press should be completely dry before the thermochromic ink is added to the press.

The fountain solution must also be removed from the fountain, rollers and the plate being used if there is any solution on them. This should be done with tap water to clean the components of solution, and then rinsed with distilled water.

NEW FOUNTAIN SOLUTION

DISTILLED WATER should be used instead of a regular fountain solution. If normal solution is used, the chemicals in the solution and the acidity of the solution will destroy the color change characteristics of the thermochromic. TO OUR KNOWLEDGE, THE USE OF DISTILLED WATER AS A FOUNTAIN SOLUTION, HAS NEVER BEEN DONE BEFORE IN OFF-SET PRINTING.

In order for regular inks to perform correctly in a lithographic process, the fountain solution must include a variety of compounds that are harmful to the ink. These compounds prevents scumming and emulsification of the water with the ink while running the press. (see Chemistry of the Graphic Arts) Other fountain solution additives enhance the performance of the ink. The special properties of our ink, allow it to be printed with distilled water in place of the fountain solution.

The explanation for why our ink works when printed with distilled water has to do with the properties of the thermochromic colorant being used, as well as the water that is included in our ink by virtue of the ink manufacturing process and low acid value of the vehicle. The thermochromic capsule is a melamine formaldehyde. This substance has both hydrophobic as well as hydrophilic properties, making its interaction with the ink vehicle unique.

Gum Arabic is applied to the portions of the printing plate that are not intended to receive ink. Often a small amount of gum arabic is added to the fountain solution. Gum arabic is a relatively high molecular weight and is not known to be detrimental to the thermochromic pigment. It is possible that a small amount could be added to distilled water when printing with the thermochromic inks. However, using distilled water as the fountain solution is known to work extremely well and is the current preferred embodiment and best mode of practicing the invention.

Heating

We have found in our experimentation that heating the press under certain conditions will improve the flow characteristics of the ink. By simply raising the temperature of the ink to above 90 degrees Fahrenheit will have the desired effect. This higher temperature can be achieved by putting heating tape on the ink fountain and using a forced air heater for the other rollers. Heating is not always necessary, and eventually we believe that no heating will be required, but right now it is the considered best mode of practicing the invention.

Other Solvents

We have found cyclohexane to be effective for the purposes of dispersion of the dry thermochromic powder, or for the cleaning of the press in preparation for printing the thermochromic ink. There are however several other possible options for cleaning or as reducers within the ink itself that will also be effective. We have isolated a few that work well, but many others exist. We have already discussed the classes of solvents that are deleterious.

Pattern Camouflage

One of the benefits of the thermochromic lithographic ink technology is that hidden images can be printed in documents printed with a combination of non-thermochromic and thermochromic images. The hidden image appears when the lithographic ink undergoes a color change. This is one of the more important aspects of the marketability aspects of the inks for toys, advertising and security issues. If the thermochromic and non-thermochromic inks overlap problems in shading occur, therefore, the inks are color and texture matched and laid down in a non-overlapping pattern but next to each other such that the original image appears uniform. As the thermochromic ink undergoes a color change the hidden image appears. The pattern of the image can be modified to be distracting to the user to prevent noticing subtle changes in pattern without a color-change.

We claim:

1. A method of making a solvent based ink formulation including a thermochromic pigment, wherein said thermochromic pigment is formed of microcapsules each containing reversible thermochromic coloring material which exhibits a visible change in color between a first color state and a second color state in response to a change in temperature, comprising:

a) drying a slurry including thermochromic pigment to a solids concentration between 80% and 95%;

b) mixing said dried slurry in an appropriate mixing base that has an inherent or adjusted acid value that is not harmful to said thermochromic pigment and does not include any solvents that are harmful to said thermochromic pigment thereby making a base formulation; and c) adding any desired ink components to said base formulations wherein said ink components have an inherent or adjusted acid value that is not harmful to said thermochromic pigment and do not include any solvents that are harmful to said thermochromic pigment.

2. The method of claim 1 wherein said slurry of thermochromic material is made by adding thermochromic material in powder form in an appropriate solvent and dispersing said thermochromic material by placing said solvent with said added thermochromic material in an ultrasound bath.

3. The method of claim 1 wherein said slurry of thermochromic material is an aqueous slurry.

4. The solvent based thermochromic ink formulation of claim 1 wherein components of said mixing base are selected from the group consisting of:
   a) mixing varnish;
   b) polyester resin vehicle; and
   c) colloidal dispersion resin.

5. The solvent based thermochromic ink formulation of claim 1 wherein said ink components are selected from the group consisting of:
   a) a gel vehicle;
   b) a free flow vehicle;
   c) a drying agent;
   d) a lithographic varnish;
   e) an ink wax;
   f) a polyester vehicle;
   g) polyglycol solvent;
   h) colloidal dispersion resin;
   i) water; and
   j) defoamer.

6. A thermochromic ink formulation prepared by the method of claim 1.

7. A method of correcting a solvent based ink formulation that would otherwise be harmful to a thermochromic pigment, wherein said thermochromic pigment is formed of microcapsules each containing reversible thermochromic coloring material which exhibits a visible change in color between a first color state and a second color state in response to a change in temperature, comprising:
   a) removing all solvents and compounds from said ink formulation that cause said thermochromic pigment to lose its color change characteristics;
   b) adding any desired ink components to said base formulations wherein said ink components do not include any solvents that are harmful to said thermochromic pigment.
   c) adjusted the acid value of said ink formulation such that it is not harmful to said thermochromic pigment; and
   d) incorporating said thermochromic material into said corrected ink formulation.

8. A thermochromic ink formulation prepared by the method of claim 7.

9. A thermochromic finger nail lacquer, comprising:
   a) a thermochromic material, wherein said thermochromic material is formed of microcapsules each having a grain size of about 0.5–50 microns and containing reversible thermochromic coloring material which exhibits a visible change in color between a first color state and a second color state in response to a change in temperature; and
   b) a finger nail lacquer formulation that includes no aldehydes, ketones, and diols, wherein said finger nail lacquer formulation has an inherent or adjusted acid value or pH that is neutral to said thermochromic material; and
   c) a color of said thermochromic finger nail lacquer changes in response to a change in temperature.

10. The thermochromic finger nail lacquer of claim 9 wherein the thermochromic material is dispersed by placing said formulation with said added thermochromic material in an ultrasound bath.

11. The method of applying a thermochromic finger nail lacquer of claim 9, comprising the steps of:
    a) applying a base coat color layer to the finger nail;
    b) allowing said base coat layer to dry;
    c) applying a layer of thermochromic finger nail lacquer of claim 9 over said base coat color layer;
    d) allowing said layer of thermochromic finger nail lacquer to dry; and
    e) applying a top clear coat layer over said layer of thermochromic finger nail lacquer.

12. A method of printing with a traditional offset press with a thermochromic ink, comprising the steps of:
    a) cleaning said press to remove all solvents and compounds that are harmful to said thermochromic ink from any portion of said press that will come into contact with said thermochromic ink;
    b) supplying a fountain solution that is not harmful to said thermochromic ink;
    c) supplying said thermochromic ink within said press; and
    d) using said press to print an image on a printing substrate with said thermochromic ink and said fountain solution.

13. The method of claim 12, further comprising selecting a printing substrate that has a pH that is not harmful to said thermochromic ink.

14. The method of claim 12, further comprising using distilled water as said fountain solution.

15. The image and substrate combination created by the method of claim 12.

16. A thermochromic ink for use in security documents, wherein:
    a) said thermochromic ink is permanently reversible between colorless and colored;
    b) when said thermochromic ink is printed on an at least a portion of a substrate adapted to carry printed copy, said thermochromic ink becomes visible only when said substrate is exposed to a temperature above or below a preselected temperature range; and
    c) said thermochromic ink is used in conjunction with a temperature insensitive ink.

\* \* \* \* \*